US011797846B2

(12) United States Patent
Kanada

(10) Patent No.: US 11,797,846 B2
(45) Date of Patent: *Oct. 24, 2023

(54) LEARNING ASSISTANCE DEVICE, METHOD OF OPERATING LEARNING ASSISTANCE DEVICE, LEARNING ASSISTANCE PROGRAM, LEARNING ASSISTANCE SYSTEM, AND TERMINAL DEVICE

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 388 days.

This patent is subject to a terminal disclaimer.

(21) Appl. No.: 17/130,468

(22) Filed: Dec. 22, 2020

(65) Prior Publication Data

US 2021/0110206 A1 Apr. 15, 2021

Related U.S. Application Data

(62) Division of application No. 16/123,456, filed on Sep. 6, 2018, now Pat. No. 10,902,286.

(30) Foreign Application Priority Data

Sep. 27, 2017 (JP) ................. 2017-187096

(51) Int. Cl.
*G06K 9/00* (2022.01)
*G06N 3/08* (2023.01)
(Continued)

(52) U.S. Cl.
CPC ............ *G06N 3/08* (2013.01); *G06F 18/214* (2023.01); *G06F 18/217* (2023.01);
(Continued)

(58) Field of Classification Search
CPC .......... G06N 3/08; G06N 3/042; G06N 3/045; G06N 20/00; G06F 18/214; G06F 18/217;
(Continued)

(56) References Cited

U.S. PATENT DOCUMENTS

2007/0217688 A1* 9/2007 Sabe ................... G06F 18/2148
382/226
2011/0010317 A1* 1/2011 Ito ......................... G06N 20/00
706/12

(Continued)

FOREIGN PATENT DOCUMENTS

JP 2001-319226 A 11/2001
JP 2008-46729 A 2/2008

OTHER PUBLICATIONS

Japanese Office Action for corresponding Japanese Application No. 2017-187096, dated Jul. 21, 2020, with English translation.
Notice of Allowance dated Oct. 20, 2020 in copending U.S. Appl. No. 16/123,456.
(Continued)

*Primary Examiner* — Xin Jia
(74) *Attorney, Agent, or Firm* — Birch, Stewart, Kolasch & Birch, LLP

(57) ABSTRACT

A learning assistance device acquires a plurality of learned discriminators obtained by causing learning discriminators provided in a plurality of respective terminal devices to perform learning using image correct answer data, acquires a plurality of discrimination results obtained by causing a plurality of learned discriminators to discriminate the same input image, determines the correct answer data of the input image on the basis of the plurality of discrimination results, causes the discriminator to perform learning the input image and the correct answer data, and outputs a result thereof as a new learning discriminator to each terminal device.

19 Claims, 9 Drawing Sheets

(51) Int. Cl.
    *G16H 50/70*     (2018.01)
    *G16H 30/40*     (2018.01)
    *G16H 30/20*     (2018.01)
    *G06N 20/00*     (2019.01)
    *G06F 18/214*     (2023.01)
    *G06F 18/21*     (2023.01)
    *G06N 3/042*     (2023.01)
    *G06N 3/045*     (2023.01)
    *G06V 10/774*     (2022.01)
    *G06V 10/778*     (2022.01)

(52) U.S. Cl.
    CPC ......... *G06F 18/2178* (2023.01); *G06N 3/042* (2023.01); *G06N 3/045* (2023.01); *G06N 20/00* (2019.01); *G06V 10/774* (2022.01); *G06V 10/7784* (2022.01); *G16H 30/20* (2018.01); *G16H 30/40* (2018.01); *G16H 50/70* (2018.01)

(58) Field of Classification Search
    CPC .............. G06F 18/2178; G06V 10/774; G06V 10/7784; G16H 30/20; G16H 30/40; G16H 50/70
    See application file for complete search history.

(56) References Cited

U.S. PATENT DOCUMENTS

| | | |
|---|---|---|
| 2015/0242760 A1 | 8/2015 | Miao et al. |
| 2018/0247153 A1* | 8/2018 | Ganapati .............. G02B 21/365 |
| 2019/0095760 A1 | 3/2019 | Kudo |
| 2019/0103185 A1 | 4/2019 | Kudo |

OTHER PUBLICATIONS

Notice of Allowance dated Sep. 23, 2020 in copending U.S. Appl. No. 16/123,456.

Office Action dated Mar. 27, 2020 in copending U.S. Appl. No. 16/123,456.

* cited by examiner

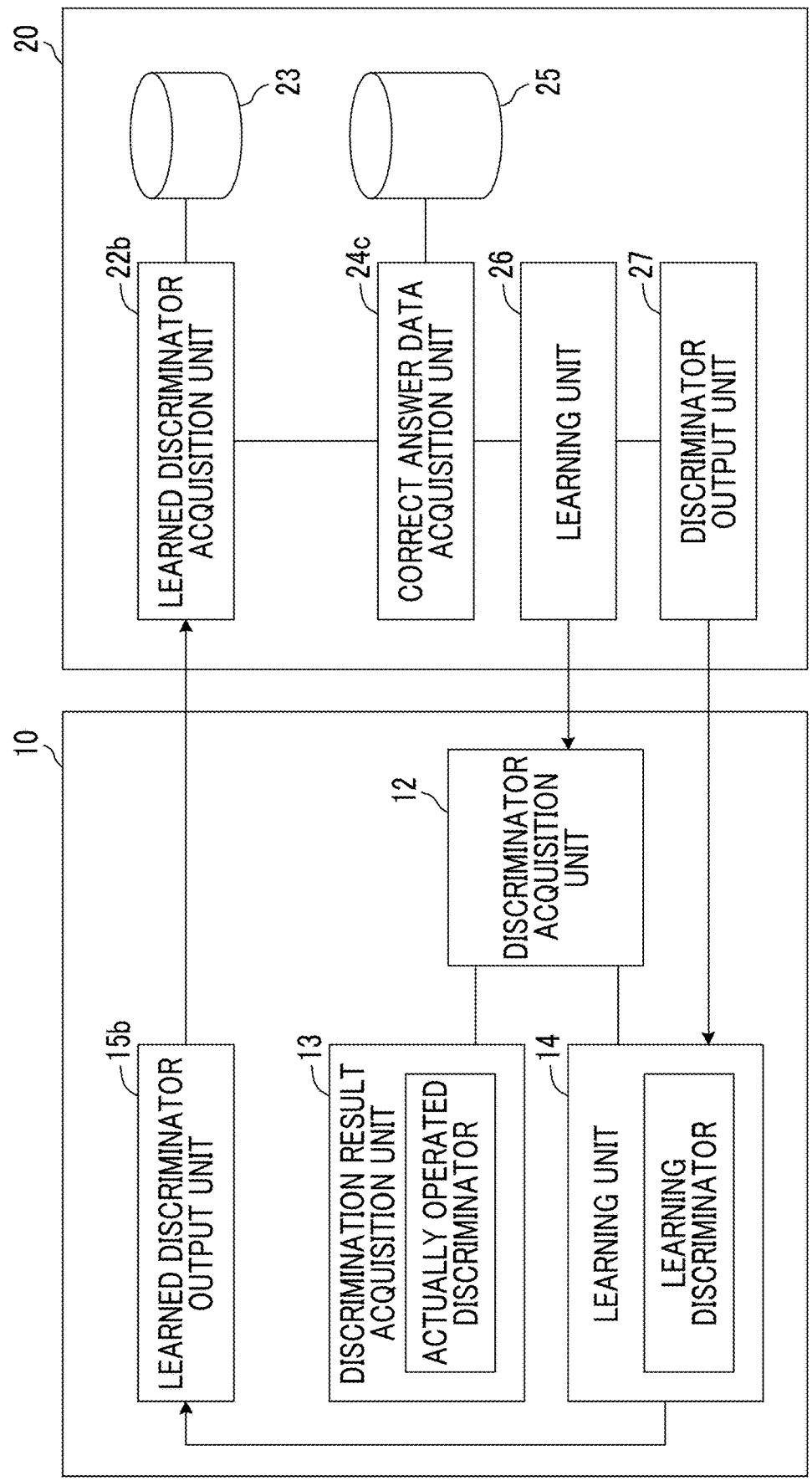

LEARNING ASSISTANCE DEVICE, METHOD OF OPERATING LEARNING ASSISTANCE DEVICE, LEARNING ASSISTANCE PROGRAM, LEARNING ASSISTANCE SYSTEM, AND TERMINAL DEVICE

CROSS-REFERENCE TO RELATED APPLICATION

This application is a Divisional of copending U.S. patent application Ser. No. 16/123,456 filed Sep. 6, 2018, which claims priority under 35 U.S.C. § 119(a) to Japanese Patent Application No. 2017-187096, filed on Sep. 27, 2017, all of which are hereby expressly incorporated in their entirety by reference into the present application.

BACKGROUND

Field of the Invention

The present invention relates to a learning assistance device that assists in generation of a discriminator using machine learning, a method of operating the learning assistance device, a learning assistance program, a learning assistance system, and a terminal device.

Related Art

In the related art, machine learning has been used to learn features of data and perform recognition or classification of images or the like. In recent years, various learning schemes have been developed, a processing time has been shortened due to an improved processing capability of a computer, and deep learning in which a system learns features of image data or the like at a deeper level can be performed. By performing the deep learning, features of images or the like can be recognized with very high accuracy, and improvement of performance of discrimination is expected.

In the medical field, artificial intelligence (AI) that recognizes features of images with high accuracy by performing learning using deep learning is desired. For deep learning, it is indispensable to perform learning using a large amount of high quality data according to purposes. Therefore, it is important to prepare learning data efficiently. Image data of a large number of cases of disease is accumulated in each medical institution with the spread of a picture archiving and communication system (PACS). Therefore, learning using image data of various cases of disease accumulated in each medical institution is considered.

Further, in recent years, a technical level of artificial intelligence has been improving in a variety of fields, and the artificial intelligence is incorporated into a variety of services and started to be used and utilized. In particular, services provided to various edge terminals over a network are increasing. For example, JP2008-046729A discloses a device in which a learning model is incorporated into a moving image topic division device that automatically divides a moving image at a switching point of a topic. JP2008-046729A discloses that the learning model has been distributed to a client terminal, the topic division is automatically executed using the distributed learning model at each client terminal, and content corrected by a user for a result of the automatic topic division is fed back for updating of the learning model. After the feedback corrected by the user is accumulated in an integration module over a network, a learning model reconstructed using the accumulated feedback is distributed to each client terminal over the network again.

However, in the medical field, since data to be learned is medical data of a patient, confidentiality is very high, and it is necessary to handle data carefully for use as learning data. Further, correct answer data is not attached to image data. Alternatively, even in a case where there is the correct answer data, the correct answer data is often managed without being associated with original image data. Therefore, it is difficult and costly to efficiently collect learning data to which the correct answer data is added.

SUMMARY

Therefore, in order to solve the above-described problems, an object of the present invention is to provide a learning assistance device which enables learning of a large amount and a variety of learning data necessary for deep learning in a medical field, a method of operating the learning assistance device, a learning assistance program, a learning assistance system, and a terminal device.

A learning assistance device of the present invention comprises: a learned discriminator acquisition unit that acquires a plurality of learned discriminators obtained by causing each of learning discriminators provided in a plurality of respective terminal devices to perform learning using an image and correct answer data thereof; and a discriminator output unit that acquires a plurality of discrimination results obtained by causing each of the plurality of learned discriminators to discriminate the same input image, determines correct answer data of the input image on the basis of the plurality of discrimination results, and outputs a new learning discriminator obtained by causing the learning discriminator to perform learning again using the input image and the determined correct answer data, wherein the learning assistance device repeatedly performs a process in which the learning discriminator acquisition unit acquires the plurality of learned discriminators obtained by causing the each of learning discriminators, the each of learning discriminators being output from the discriminator output unit and being provided for each of the plurality of terminal devices, to perform learning using an image and correct answer data thereof, and the discriminator output unit determines a new correct answer data of a new same input image different from the input image on the basis of a plurality of discrimination results obtained by causing the plurality of learned discriminators acquired by the learned discriminator acquisition unit to discriminate the new same input image, and outputs a new learning discriminator obtained by causing the learning discriminator output by the discriminator output unit to perform learning again using the new input image and the determined new correct answer data.

A method of operating a learning assistance device of the present invention is a method of operating a learning assistance device including a learned discriminator acquisition unit and a discriminator output unit, the method comprising: acquiring a plurality of learned discriminators obtained by causing each of learning discriminators provided in a plurality of respective terminal devices to perform learning using an image and correct answer data thereof by the learned discriminator acquisition unit; acquiring a plurality of discrimination results obtained by causing each of the plurality of learned discriminators to discriminate the same input image, determines correct answer data of the input image on the basis of the plurality of discrimination results, and outputs a new learning discriminator obtained by causing the learning discriminator to perform learning again using the input image and the determined correct answer data by the discriminator output unit; and repeatedly performing a process in which the learned discriminator acquisition unit acquires the plurality of learned discriminators obtained by causing the each of learning discriminators, the each of learning discriminators being output from the discriminator output unit and being provided for each of the plurality of terminal devices, to perform learning using an image and correct answer data thereof, and the discriminator output unit determines a new correct answer data of a new same input image different from the input image on the basis of a plurality of discrimination results obtained by causing the plurality of learned discriminators acquired by the learned discriminator acquisition unit to discriminate the new same input image, and outputs a new learning discriminator obtained by causing the learning discriminator output by the discriminator output unit to perform learning again using the new input image and the determined new correct answer data.

A learning assistance program according to the present invention causes a computer to function as: a learned discriminator acquisition unit that acquires a plurality of learned discriminators obtained by causing each of learning discriminators provided in a plurality of respective terminal devices to perform learning using an image and correct answer data thereof; and a discriminator output unit that acquires a plurality of discrimination results obtained by causing each of the plurality of learned discriminators to discriminate the same input image, determines correct answer data of the input image on the basis of the plurality of discrimination results, and outputs a new learning discriminator obtained by causing the learning discriminator to perform learning again using the input image and the determined correct answer data, wherein the program causes a process in which the learned discriminator acquisition unit acquires the plurality of learned discriminators obtained by causing the each of learning discriminators, the each of learning discriminators being output from the discriminator output unit and being provided for each of the plurality of terminal devices, to perform learning using an image and correct answer data thereof, and the discriminator output unit determines a new correct answer data of a new same input image different from the input image on the basis of a plurality of discrimination results obtained by causing the plurality of learned discriminators acquired by the learned discriminator acquisition unit to discriminate the new same input image, and outputs a new learning discriminator obtained by causing the learning discriminator output by the discriminator output unit to perform learning again using the new input image and the determined new correct answer data, to be repeatedly performed.

"Acquire a learned discriminator" may be acquiring the learned discriminator or may be receiving a parameter of the discriminator and setting the parameter in a prepared discriminator to acquire the learned discriminator. For example, in a case where the discriminator is a multilayered neural network, a program in which a learned multilayered neural network is incorporated may be acquired or a weight of coupling between layers of units of the multilayered neural network may be acquired as a parameter and the parameter may be set in the prepared multilayered neural network, so that the learned multilayered neural network can be acquired.

Further, the discriminator output unit further outputs an actually operated discriminator learning the image and the correct answer data thereof used for learning by the new learning discriminator.

The "actually operated discriminator" is a discriminator capable of acquiring a discrimination result of input image data, which cannot perform additional learning, and the "learning discriminator" is a discriminator that can perform additional learning using an image and correct answer data of the image. Further, the actually operated discriminator to be output is a discriminator caused to perform learning using an image and correct answer data of the image that are all the same as the image and the correct answer data of the image learned by the output learning discriminator.

Further, the learned discriminator acquisition unit may acquire the learned discriminator from the plurality of terminal devices over a network, and the discriminator output unit may output the new learning discriminator to the plurality of terminal devices over the network.

Further, the discriminator output unit may determine a discrimination result having the largest number of same results among the plurality of discrimination results, as correct answer data of the input image.

Further, the discriminator output unit may determine a weight of each of the plurality of learned discriminators according to the terminal device learned by the learned discriminator, adds the weights of the learned discriminators having the same result among the discrimination results, and sets a discrimination result having the largest added weight as correct answer data of the input image.

Further, the discriminator output unit may determine the weight of each of the learned discriminators learned at each of the terminal devices according to the number of pieces of correct answer data learned by the learned discriminator at each terminal device, add the weights of the learned discriminators having the same discrimination result, and set a discrimination result having the largest added weight as correct answer data of the input image.

Further, the discriminator output unit may determine weights for types of cases of disease of the image learned by the respective learned discriminators with respect to the respective learned discriminators, add the weights corresponding to the types of cases of disease of the input image in the learned discriminator having the same discrimination result, and set a discrimination result having the largest added weight as correct answer data of the input image.

Further, the learning assistance device may further comprise an evaluation unit that evaluates a correct answer rate using an image set including a plurality of images serving as a reference with respect to the plurality of learned discriminators, wherein the discriminator output unit may determine the weight of each of the plurality of learned discriminators according to the correct answer rate obtained by the evaluation unit, add the weights of the respective learned discriminators having the same discrimination results, and set the discrimination result having the largest added weight as correct answer data of the input image.

A learning assistance system according to the present invention is a learning assistance system in which a learning assistance device and a plurality of terminal devices are connected over a network, wherein the terminal device includes a learned discriminator output unit that outputs a learned discriminator obtained by causing a learning discriminator to perform learning using an image and correct answer data thereof over the network, the learning assistance device includes a learned discriminator acquisition unit that acquires a plurality of learned discriminators from the plurality of terminal devices over the network, and a discriminator output unit that acquires a plurality of discrimination results obtained by causing the plurality of learned discriminators to discriminate the same input image, determines correct answer data of the input image on the basis of the plurality of discrimination results, and outputs a new learning discriminator obtained by causing the learning discriminator to perform learning again using the input image and the determined correct answer data to the plurality of terminal devices over the network, and the terminal device includes a discriminator acquisition unit that receives the learning discriminator output from the learning assistance device over the network.

Further, in the learning assistance system, the discriminator acquisition unit may further acquire an actually operated discriminator learning the same image and correct answer data of the image as those of the learning discriminator output from the learning assistance device over a network, and the terminal device may further include a discrimination result acquisition unit that acquires a discrimination result of discriminating an image that is a discrimination target using the actually operated discriminator.

A terminal device according to the present invention comprises a discriminator acquisition unit that acquires a learning discriminator, and a learned actually operated discriminator learned using the same image and correct answer data of the image as those of the learning discriminator; a discrimination result acquisition unit that acquires a discrimination result of discriminating an image that is a discrimination target using the actually operated discriminator; and a learned discriminator output unit that outputs a learned discriminator obtained by causing the learning discriminator to perform learning using an image and correct answer data thereof.

Further, in the terminal device, the discriminator acquisition unit may acquire the learning discriminator and the actually operated discriminator from a learning assistance device over a network, and the learned discriminator output unit may send and output the learned discriminator over the network.

Another learning assistance device of the present invention comprises a memory that stores instructions to be executed by a computer, and a processor configured to execute the stored instructions, wherein the processor executes an acquisition process of acquiring a plurality of learned discriminators obtained by causing each of learning discriminators provided in a plurality of respective terminal devices to perform learning using an image and correct answer data thereof, and an output process of acquiring a plurality of discrimination results obtained by causing each of the plurality of learned discriminators to discriminate the same input image, determining correct answer data of the input image on the basis of the plurality of discrimination results, and outputting a new learning discriminator obtained by causing the learning discriminator to perform learning again using the input image and the determined correct answer data, and the learning assistance device repeatedly performs a process of acquiring the plurality of learned discriminators obtained by causing the each of learning discriminators, the each of learning discriminators being output from the discriminator output unit and being provided for each of the plurality of terminal devices, to perform learning using an image and correct answer data thereof, determining a new correct answer data of a new same input image different from the input image on the basis of a plurality of discrimination results obtained by causing the plurality of learned discriminators acquired by the learned discriminator acquisition unit to discriminate the new same input image, and outputting a new learning discriminator obtained by causing the learning discriminator output by the discriminator output unit to perform learning again using the new input image and the determined new correct answer data.

According to the present invention, the learning assistance device acquires the plurality of learned discriminators obtained by causing learning discriminators provided in a plurality of respective terminal devices to perform learning using image correct answer data, acquires the plurality of discrimination results of discriminating the same input image, determines the correct answer data of the input image on the basis of the plurality of discrimination results, and causes the discriminator to perform learning using the input image and the determined correct answer data. Therefore, it is possible to automatically generate the data for learning from the image to which the correct answer data is not attached, perform deep learning using a large amount of images, and improve performance of discrimination.

BRIEF DESCRIPTION OF THE DRAWINGS

FIG. 9 is a block diagram illustrating a schematic configuration of a terminal device and a learning assistance device according to a fourth embodiment.

DETAILED DESCRIPTION

Figure 1:
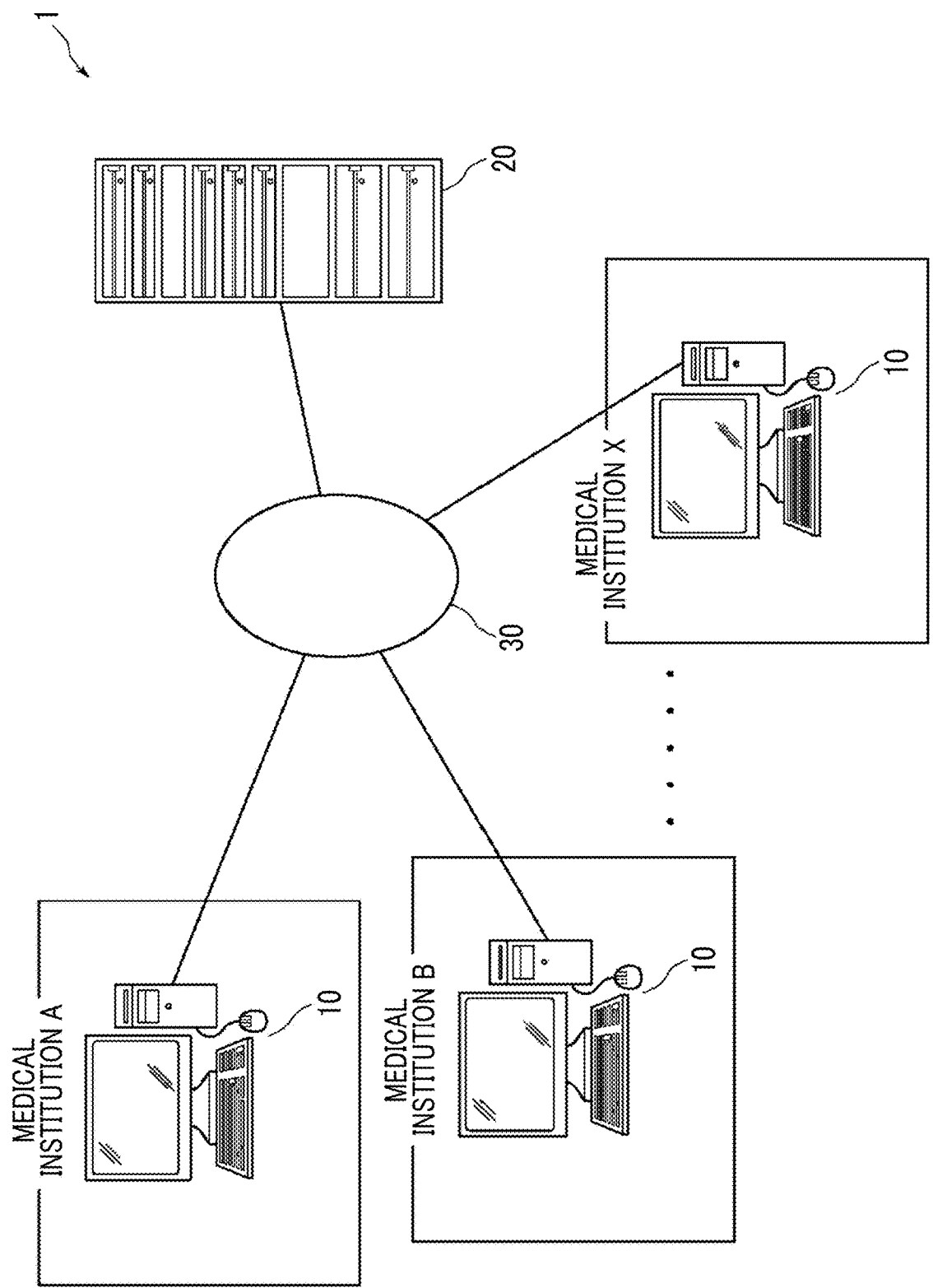
FIG. 1 is a diagram illustrating a schematic configuration of a learning assistance system of the present invention.

FIG. 1 illustrates a schematic configuration of a learning assistance system 1 according to a first embodiment of the present invention. The learning assistance system 1 is configured by connecting a plurality of terminal devices 10 installed in a plurality of medical institutions A, B, . . . , X and a learning assistance device 20 placed on a cloud side over a network 30.

The learning assistance device 20 includes a well-known hardware configuration such as a central processing unit (CPU), a memory, a storage, an input and output interface, a communication interface, an input device, a display device, and a data bus, and is a high-performance computer in which a well-known operation system or the like is installed and which has a server function. Further, a graphics processing unit (GPU) may be provided, as necessary. Alternatively, the learning assistance device 20 may be a virtualized virtual server provided using one or a plurality of computers. The learning assistance program of the present invention is installed in a server, and functions as a learning assistance device by a program instruction being executed by the CPU of the computer.

The terminal device 10 is a computer for image processing provided in the respective medical institutions A, B, . . . , X, and includes a well-known hardware configuration such as a CPU, a memory, a storage, an input and output interface, a communication interface, an input device, a display device, and a data bus. A well-known operation system or the like is installed in the terminal device 10. The terminal device 10 includes a display as a display device. Further, a GPU may be provided, as necessary.

The network 30 is a wide area network (WAN) that widely connects the terminal devices 10 placed at the plurality of medical institutions A, B, . . . , X to the learning assistance device 20 via a public network or a private network.

Figure 2:
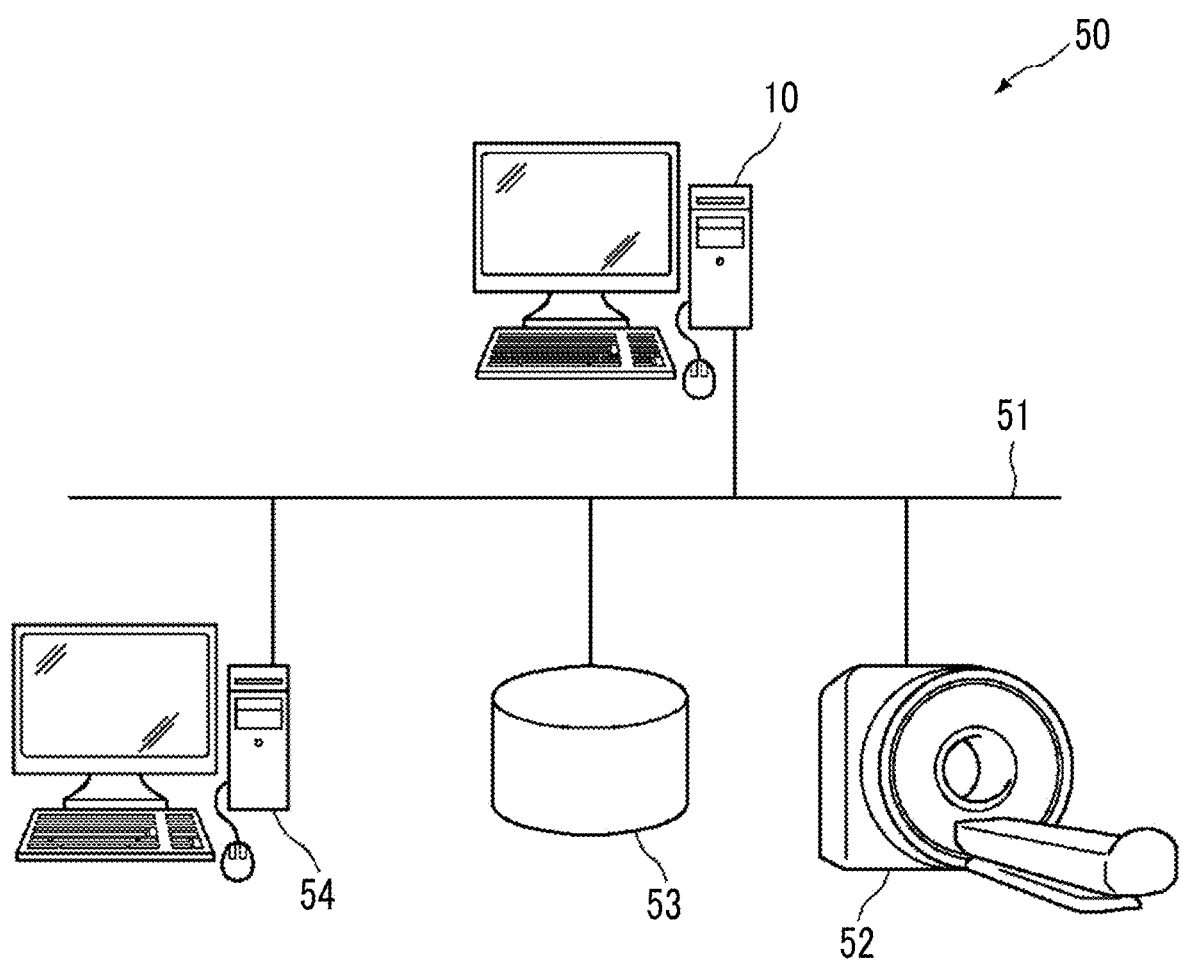
FIG. 2 is a diagram illustrating a schematic configuration of a medical information system.

Further, as illustrated in FIG. 2, the terminal device 10 is connected to respective medical information systems 50 of the respective medical institutions A, B, . . . , X over a local area network (LAN) 51. The medical information system 50 includes a modality (an imaging device) 52, an image database 53, and an image interpretation medical workstation 54, and is configured so that transmission and reception of image data to and from each other are performed over the network 51. It should be noted that in the network 51, it is desirable to use a communication cable such as an optical fiber so that image data can be transferred at a high speed.

The modality 52 includes a device that images an examination target part of a subject to generate an examination image representing the part, adds accessory information defined in a DICOM standard to the image, and outputs the resultant image. Specific examples of the device include a computed tomography (CT) device, a magnetic resonance imaging (MRI) device, a positron emission tomography (PET) device, an ultrasonic device, and a computed radiography (CR) device using a planar X-ray detector (FPD: flat panel detector).

In the image database 53, a software program for providing a function of a database management system (DBMS) is incorporated in a general-purpose computer, and a large capacity storage is included. This storage may be a large capacity hard disk device, or may be a disk device connected to a network attached storage (NAS) or a storage area network (SAN) connected to the network 51. Further, the image data captured by the modality 52 is transmitted to and stored in the image database 53 over the network 51 according to a storage format and a communication standard conforming to a DICOM standard.

The image interpretation medical workstation 54 is a computer that is used for an image interpretation doctor of a radiology department to interpret an image and create an interpretation report. The image interpretation medical workstation 54 performs a display of the image data received from the image database 53 and performs automatic detection of a portion likely to be a lesion in the image.

In the embodiment, a case where an image processing program in which a discriminator functioning as an actually operated discriminator is incorporated in each terminal device 10 is provided from the learning assistance device 20, and a learning program in which a discriminator functioning as a learning program separately from the image processing program is incorporated is provided will be described. The image processing program and the learning program distributed to each terminal device 10 are installed in the terminal device 10 to function as an image processing device in which the actually operated discriminator is incorporated, and a learning discriminator.

Further, a case where the actually operated discriminator and the learning discriminator are multilayered neural networks subjected to deep learning to be able to discriminate a plurality of types of organ areas and/or lesion areas will be described. In the multilayered neural network, a calculation process is performed on a plurality of pieces of different calculation result data obtained by a preceding layer for input data, that is, extraction result data of a feature amount using various kernels in each layer, data of the feature amount obtained by the calculation process is acquired, and a further calculation process is performed on the data of the feature amount in the next and subsequent processing layers. Thus, it is possible to improve a recognition rate of the feature amount and to discriminate which of a plurality of types of areas the input image data is.

Figure 3:
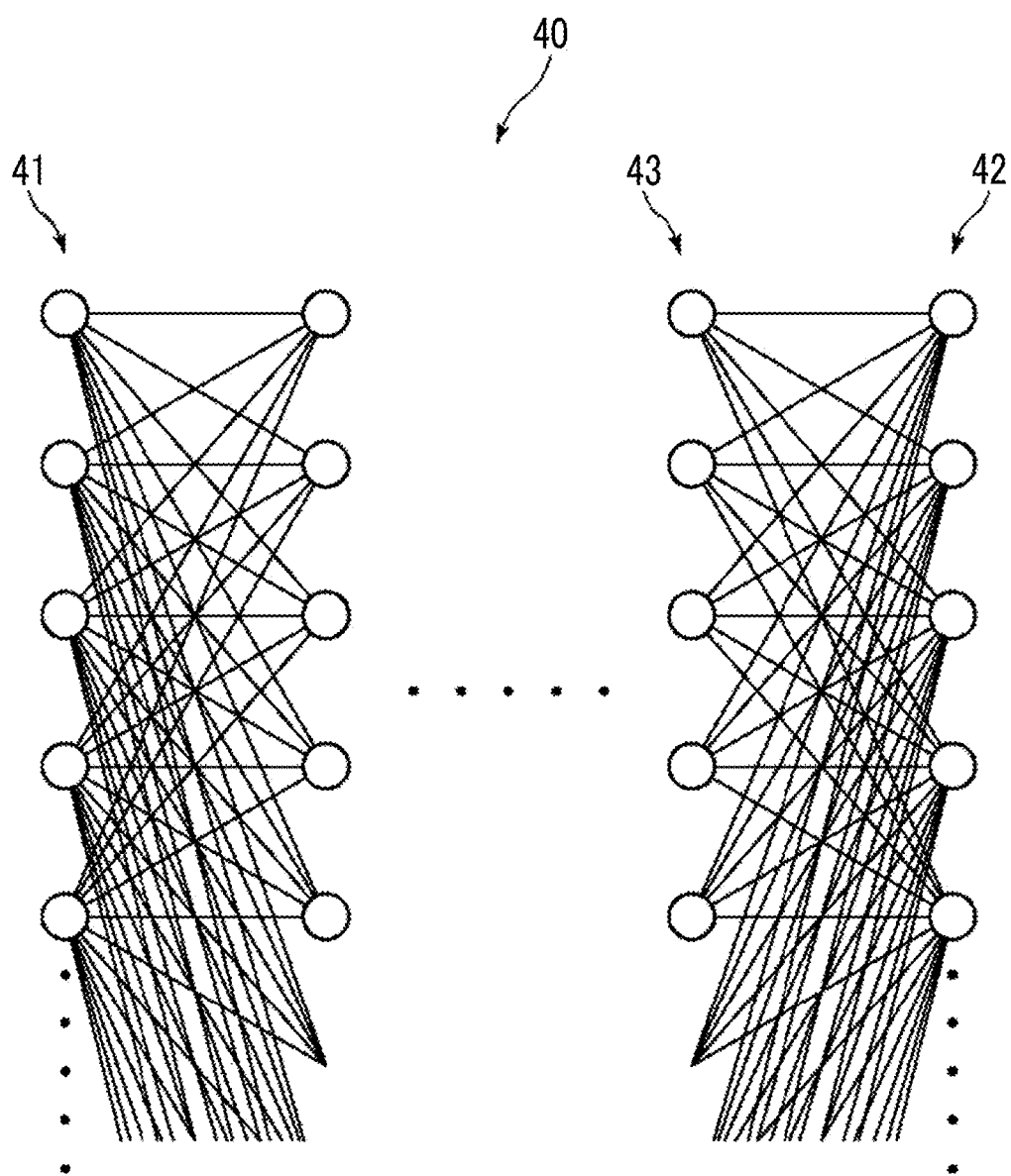
FIG. 3 illustrates an example of a multilayered neural network.

FIG. 3 is a diagram illustrating an example of the multilayered neural network. As illustrated in FIG. 3, the multilayered neural network 40 includes a plurality of layers including an input layer 41 and an output layer 42. In FIG. 3, a layer before the output layer 42 is denoted by reference numeral 43.

In the multilayered neural network 40, the image data is input to the input layer 41 and a discrimination result of an area is output. In a case where learning is performed, the output discrimination result is compared with correct answer data, and a weight of coupling between the respective layers of units (indicated by circles in FIG. 3) included in the respective layers of the multilayered neural network 40 is corrected from the output side (the output layer 42) to the input side (the input layer 41) according to whether an answer is a correct answer or an incorrect answer. The correction of the weight of coupling is repeatedly performed a predetermined number of times, or is repeatedly performed until a correct answer rate of the output discrimination result is 100% or is equal to or greater than a predetermined threshold value using a large number of pieces of image data with correct answer data, and the learning ends.

Figure 4:
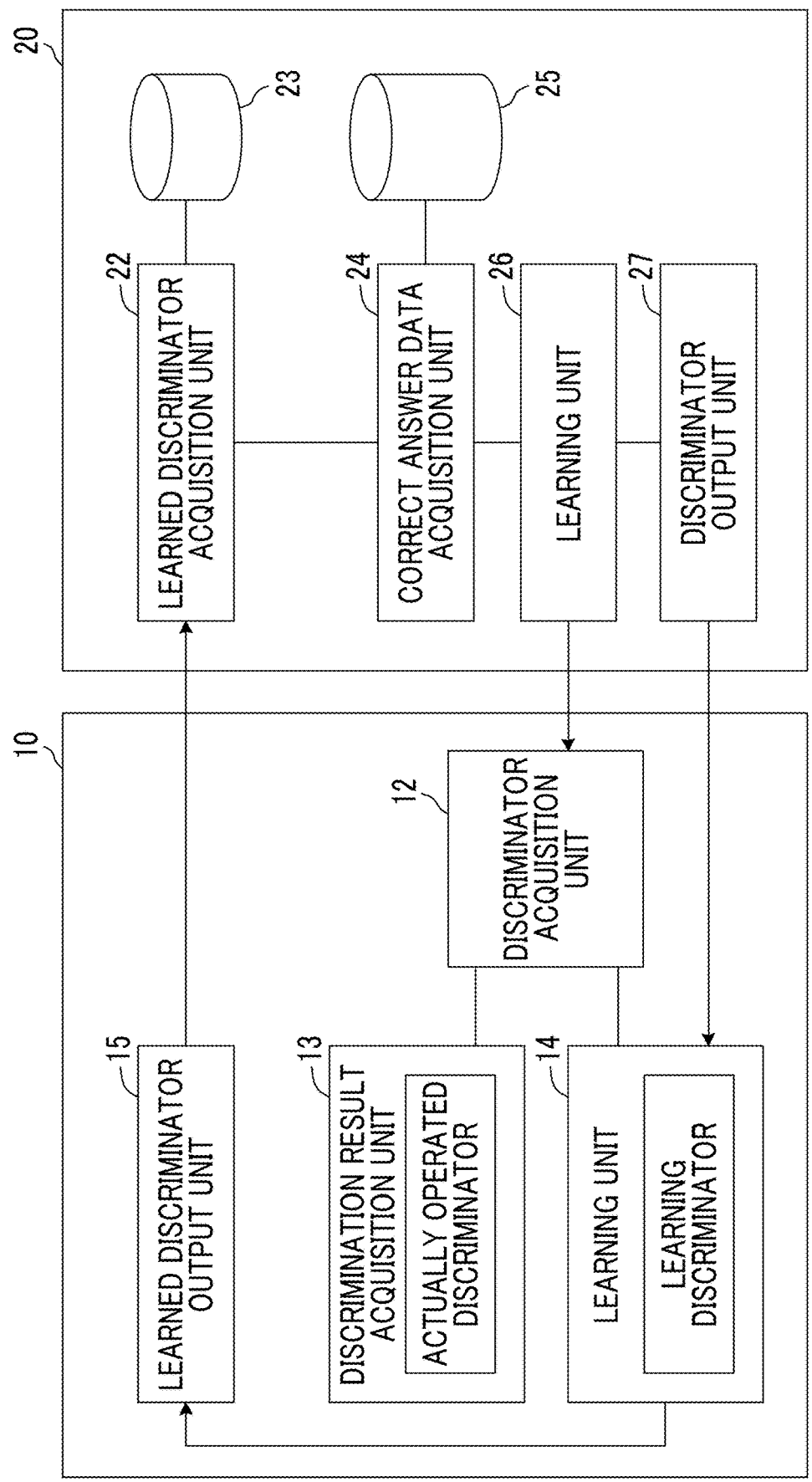
FIG. 4 is a block diagram illustrating a schematic configuration of a terminal device and a learning assistance device according to a first embodiment.

FIG. 4 is a block diagram illustrating a schematic configuration of the terminal device 10 and the learning assistance device 20. Functions of the terminal device 10 and the learning assistance device 20 will be described in detail with reference to FIG. 4. First, the terminal device 10 will be described.

The terminal device 10 includes a discriminator acquisition unit 12, a discrimination result acquisition unit 13, a learning unit 14, and a learned discriminator output unit 15.

The discriminator acquisition unit 12 acquires a learning discriminator and an actually operated discriminator. For example, the image processing program and the learning program are received from the learning assistance device 20 over the network 30, and the received image processing program is installed. Accordingly, image processing in which the actually operated discriminator is incorporated becomes executable in the terminal device 10 and functions as the discrimination result acquisition unit 13. Similarly, the learning program is installed, and the learning discriminator becomes executable and functions as the learning unit 14. It should be noted that the learning discriminator is a discriminator that has learned the same image correct answer data as the actually operated discriminator received from the learning assistance device 20. In the following description, the image processing in which the actually operated discriminator is incorporated is simply referred to as an actually operated discriminator. It should be noted that the image correct answer data refers to a combination of the image data and correct answer data thereof. Details of the image correct answer data will be described below.

The discrimination result acquisition unit 13 inputs a discrimination target image data to the actually operated discriminator and acquires a discrimination result. The actually operated discriminator is a discriminator of which discrimination performance has been guaranteed in the learning assistance device 20, and in each of the medical institutions A, B, . . . , X, the discrimination is performed on the image data that is a diagnosis target using the actually operated discriminator. Further, the discrimination result acquisition unit 13 may perform discrimination of the image data that is a diagnosis target sent from the image interpretation medical workstation 54 to the terminal device 10 over the network 51, and transmit a discrimination result from the terminal device 10 to the image interpretation medical workstation 54.

The learning unit 14 causes the learning discriminator to perform learning using the image data and the correct answer data thereof. The correct answer data includes a mask image showing an area such as an organ or abnormal shadow of the image data, and information indicating what the area of the mask image is (for example, an area of an organ such as a liver, a kidney, or a lung or an area of an abnormal shadow such as a liver cancer, a kidney cancer, or a pulmonary nodule).

The correct answer data may be created by an image interpretation doctor or the like of each of the medical institutions A, B, . . . , X observing the image data. For example, the image data is extracted from the image database 53, the discrimination result acquisition unit 13 inputs the image data to the actually operated discriminator and acquires a discrimination result, and a user such as the image interpretation doctor determines whether the discrimination result is a correct answer or an incorrect answer, and stores a discrimination result together with the input image data and correct answer data in the image database 53 as image correct answer data in the case of the correct answer. In the case of an incorrect answer, the user generates a mask image of the correct answer data, assigns the correct answer data to the image data, and stores the resultant data in the image database 53 as image correct answer data.

Therefore, the learning unit 14 causes the multilayered neural network 40 of the learning discriminator to perform learning using a large number of pieces of image correct answer data stored in the image database 53. First, the image data of the image correct answer data is input to the multilayered neural network 40, and a discrimination result is output. Then, the output discrimination result is compared with the correct answer data, and a weight of coupling between the respective layers of the units included in the respective layers of the multilayered neural network 40 from the output side to the input side is corrected according to whether the answer is a correct answer or an incorrect answer. The correction of the weight of the coupling is repeatedly performed using a large number of pieces of correct answer data a predetermined number of times or until the correct answer rate of the output discrimination result becomes 100%, and the learning is ended.

The learned discriminator output unit 15 outputs the learning discriminator of which the learning has ended in the learning unit 14 as a learned discriminator. Specifically, the weight (hereinafter referred to as a parameter) of coupling between the layers of the units constituting the neural network constituting the learned discriminator is periodically transmitted to the learning assistance device 20 over the network 30.

Next, the learning assistance device 20 will be described. As illustrated in FIG. 4, the learning assistance device 20 includes a learned discriminator acquisition unit 22, a discriminator storage unit 23, a correct answer data acquisition unit 24, a correct answer data storage unit 25, a learning unit 26, and a discriminator output unit 27.

The learned discriminator acquisition unit 22 receives a parameter of the multilayered neural network 40 constituting the learned discriminators transmitted from the plurality of terminal devices 10 over the network 30. The received parameter is temporarily stored in the discriminator storage unit 23. The multilayered neural network 40 is provided in the learning assistance device 20 in advance and the parameter received from each terminal device 10 is set as the weight of the coupling between the respective layers of the units of the multilayered neural network 40 provided in the learning assistance device 20. By re-setting the parameter received from each terminal device in this weight, the same learned discriminator as each terminal device 10 can be acquired.

The correct answer data acquisition unit 24 causes each of the learned discriminators collected from each of the terminal devices 10 to discriminate the same input image data to acquire a plurality of discrimination results, and determines the correct answer data of the input image data from the plurality of discrimination results.

A large number of pieces of image data are often stored in a database without correct answer data attached thereto. In order to attach the correct answer data to the image data, for example, the image data is input to the discriminator so as to acquire a discrimination result, and a user such as an image interpretation doctor performs a determination that the answer is a correct answer or an incorrect answer with respect to the discrimination result, and registers the discrimination result as the image correct answer data in association with the correct answer data and the input image data in the case of the correct answer. In case of the incorrect answer, the user creates a mask image of the correct answer data and registers the mask image as image correct answer data in association with input image data. Work of creating the correct answer data in this way is laborious and it is difficult to manually generate a large number of pieces of correct answer data.

Therefore, the correct answer data acquisition unit 24 determines the largest number of same discrimination results as correct answer data of the input image data from the discrimination results obtained by inputting the same input image data to the learned discriminators collected from the respective terminal devices 10. Thus, in a case where the correct answer data is determined from a plurality of discrimination results obtained by using the learned discriminators collected from the respective terminal devices 10, accurate correct answer data can be automatically generated, and therefore, it is possible to easily obtain a large number of pieces of correct answer data. The obtained correct answer data is accumulated in the storage (the correct answer data storage unit 25) as image correct answer data in association with the input image data.

The learning unit 26 is provided with a deep learning discriminator configured of a multilayered neural network 40. The image correct answer data accumulated in the correct answer data storage unit 25 is sequentially input to the deep learning discriminator, so that learning is performed.

In a stage the learning had progressed to a certain extent and accuracy of the discrimination of the deep learning discriminator has improved, the discriminator output unit 27 generates an image processing program (actually operated discriminator) incorporating the deep learning discriminator learned by the learning unit 26 and a learning program (the learning discriminator), and distributes the programs to each terminal device 10 over the network 30. Since software intended for medical purposes is a target of the Pharmaceutical and Medical Device Act (the revised Pharmaceutical Affairs Act), the software is required to meet a criterion prescribed in the Pharmaceutical and Medical Device Act. Therefore, it is preferable to confirm that a deep learning discriminator before distribution exceeds an evaluation standard using an evaluation image set formed through a combination of a plurality of images in which the criterion prescribed in the Pharmaceutical and Medical Device Act can be evaluated, and then, distribute deep learning discriminator.

Even after the discriminator output unit 27 distributes the image processing program and the learning program to the respective terminal devices 10, the learning unit 26 sequentially inputs the image correct answer data accumulated in the correct answer data storage unit 25 to the deep learning discriminator as it is and causes the deep learning discriminator to perform learning. That is, the learning unit 26 causes the learning discriminator output by the discriminator output unit 27 to perform additional learning, and the discriminator output unit 27 outputs the additionally learned learning discriminator as a new learning discriminator.

Figure 5:
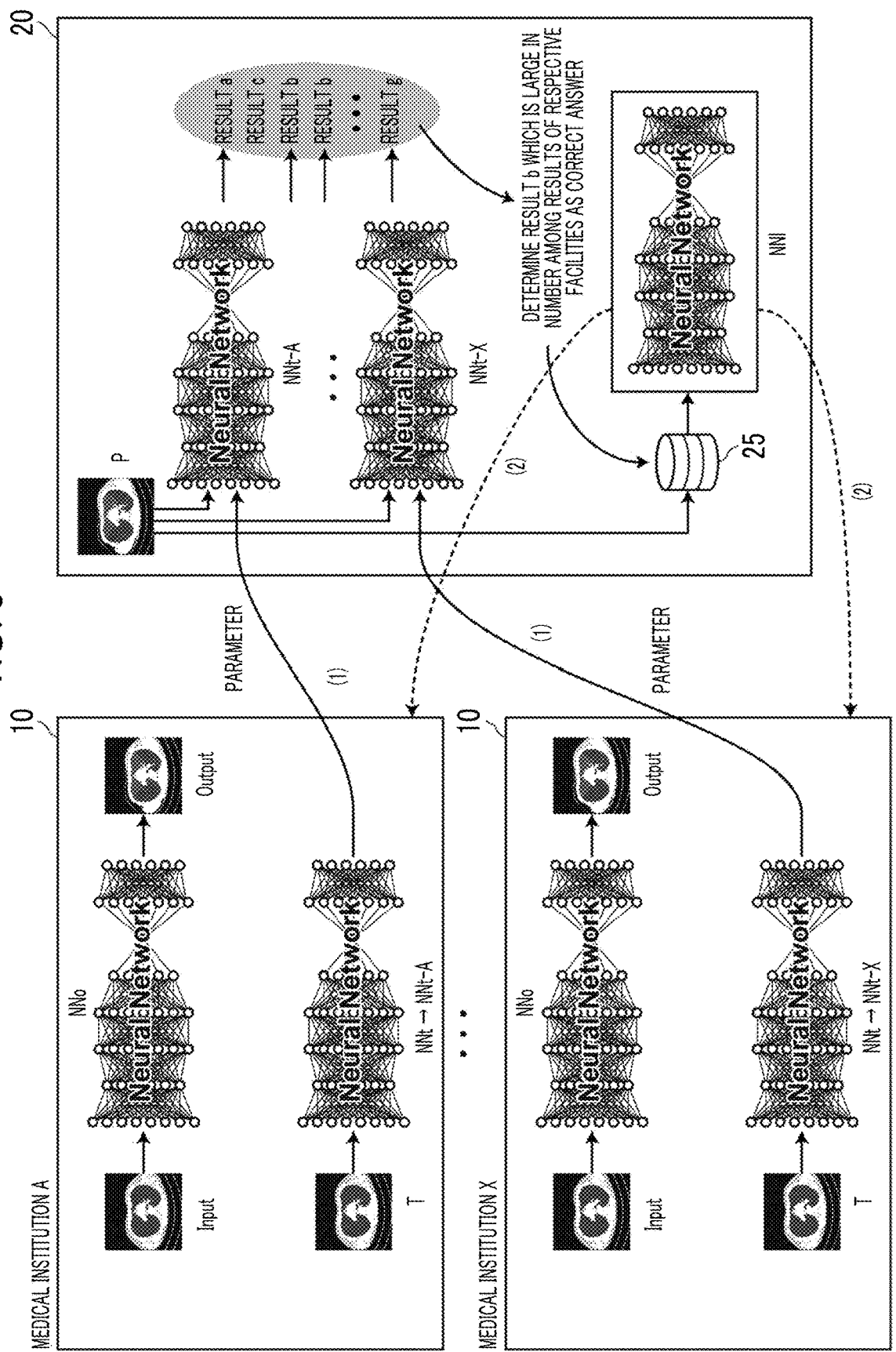
FIG. 5 is a diagram illustrating learning of a discriminator.
Figure 6:
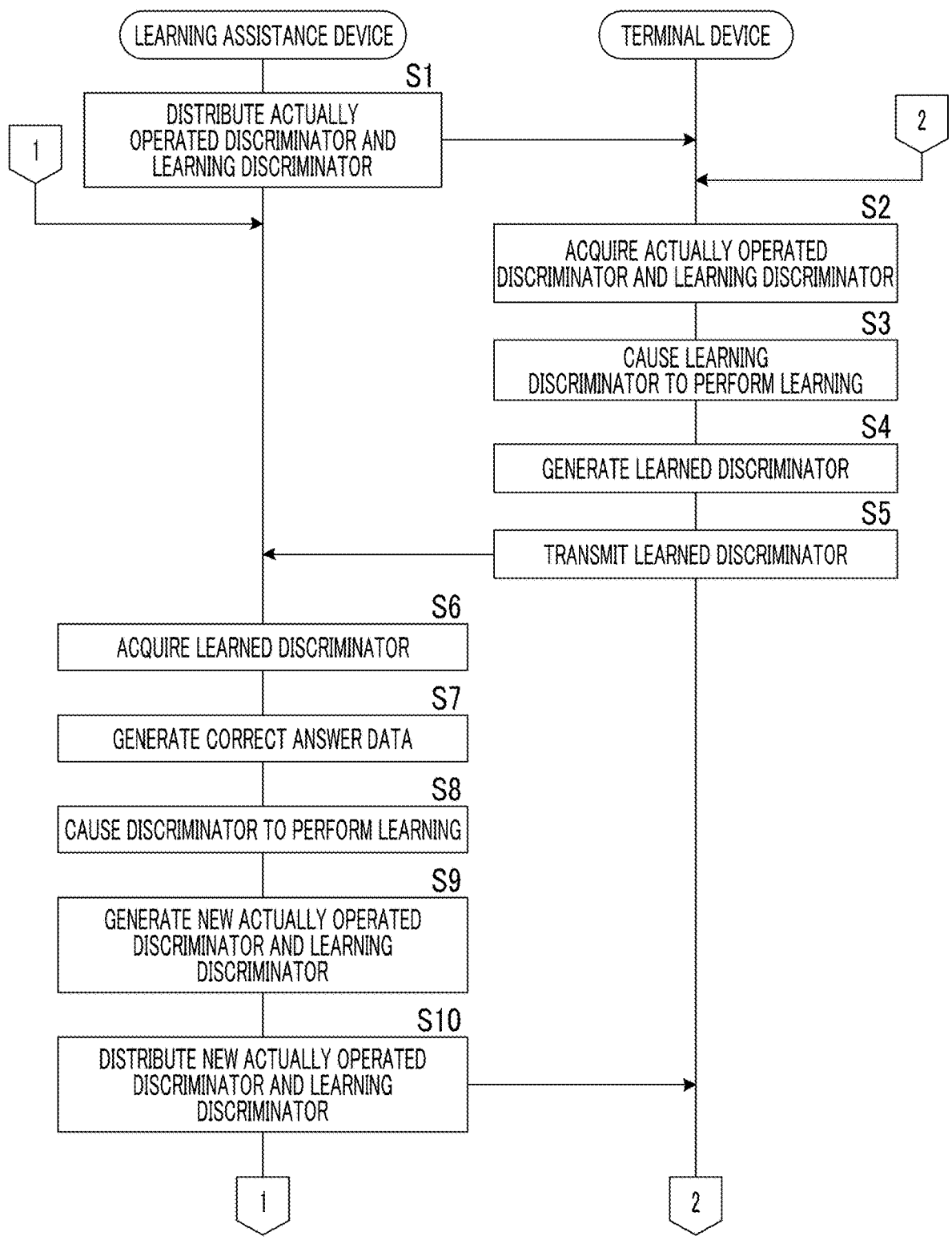
FIG. 6 is a flowchart showing a flow of a process of causing the discriminator to perform learning.

Next, a flow of a deep learning process of the embodiment will be described with reference to a transition diagram of FIG. 5 and a flowchart of FIG. 6.

First, in the learning assistance device 20, the discriminator output unit 27 distributes the actually operated discriminator NNo and the learning discriminator NNt to the plurality of terminal devices 10, and to the medical institution A, . . . , the medical institution X over the network 30 (S1).

In the terminal device 10, the discriminator acquisition unit 12 acquires the actually operated discriminator NNo and the learning discriminator NNt (S2). The actually operated discriminator NNo is used for diagnosis by an image interpretation doctor, and the discrimination result acquisition unit 13 discriminates image data (input) that is a diagnosis target and obtains a discrimination result (output) (see FIG. 5). Further, in the medical institution A, the learning unit 14 of the terminal device 10 causes the learning discriminator NNt to perform learning using the image correct answer data T stored in the image database 53 (S3) and generates the learned discrimination unit NNt-A (S4). Similarly, in the medical institution X, the learning unit 14 of the terminal device 10 causes the learning discriminator NNt to perform learning using the image correct answer data T and generates the learned discriminator NNt-X (S4).

Periodically, in each terminal device 10, the learned discriminator output unit 15 transmits the learned discriminator to the learning assistance device 20 (S5). The parameter of the learned discriminator NNt-A is transmitted from the terminal device 10 of the medical institution A to the learning assistance device 20, and the parameter of the learned discriminator NNt-X is transmitted from the terminal device 10 of the medical institution X to the learning assistance device 20 (see a solid arrow (1) in FIG. 5).

In the learning assistance device 20, the learned discriminator acquisition unit 22 temporarily stores the parameters of the learned discriminators received from the plurality of terminal devices 10 in the discriminator storage unit 23. By setting this parameter in the multilayered neural network 40 provided in the learning assistance device 20, the learned discriminator learned by each terminal device 10 is acquired (S6).

The correct answer data acquisition unit 24 inputs the input image data P to the learned discriminator of each terminal device 10 to obtain the discrimination result. In the example of FIG. 5, a result a, a result b, a result c, . . . , a result g are obtained, and a largest number of results b are determined to be correct answer data of the input image data P (S7). The input image data P and the correct answer data are accumulated in the storage 25 in association with each other.

The learning unit 26 causes the deep learning discriminator NNl to perform learning using the input image data P and the result b (correct answer data) (S8). Periodically, a new version of the actually operated discriminator NNo and the learning discriminator NNt are generated on the basis of the deep learning discriminator NNl (S9). The discriminator output unit 27 distributes the new version of the actually operated discriminator NNo and learning discriminator NNt to each of the terminal devices 10 (S10; see an arrow (2) of a broken line in FIG. 5).

In the terminal device 10 of the medical institution A, the discriminator acquisition unit 12 acquires the new version of the actually operated discriminator NNo and learning discriminator NNt again (S2). The learning unit 14 of the terminal device 10 causes the new version of learning discriminator NNt to perform learning using the image correct answer data T stored in the image database 53 (S3) and generate the learned discriminator NNt-A again (S4).

In the terminal device 10 of the medical institution X, the discriminator acquisition unit 12 acquires the new version of the actually operated discriminator NNo and learning discriminator NNt again (S2). The learning unit 14 of the terminal device 10 causes the new version of learning discriminator NNt to perform learning using the image correct answer data T stored in the image database 53 (S3) and generates a learned discriminator NNt-X (S4). Consequently, the process from S5 to S10 is performed, as in the same manner as described above.

The processes of S2 to S10 are repeated, and the learning assistance device 20 generates an actually operated discriminator and a learning discriminator of which the performance has been improved while generating the correct answer data, and distributes the actually operated discriminator and the learning discriminator to the terminal device 10.

As described above, by the terminal device 10 placed in each medical institution performing learning using the image data stored in the medical institution, a discriminator improving discrimination performance is generated in each medical institution. By the learning assistance device 20 generating the correct answer data using the discriminators of which the performance have been improved in each medical institution, a large amount of accurate correct answer data can be generated, and deep Learning can be performed using this correct answer data.

Although the case where the mask image of the correct answer data for the image data has the information indicating what the area on the image is has been described above, the discriminator may be configured to (1) determine an organ area and an organ name by determining what organ each pixel position of the image data is, (2) determine a lesion area and a type of lesion by determining a type of lesion of each pixel in units of pixels of the image data. Alternatively, correct answer data for one image may be specified as a disease name or an image diagnostic name, and (3) the disease name may be specified from the image data.

Figure 7:
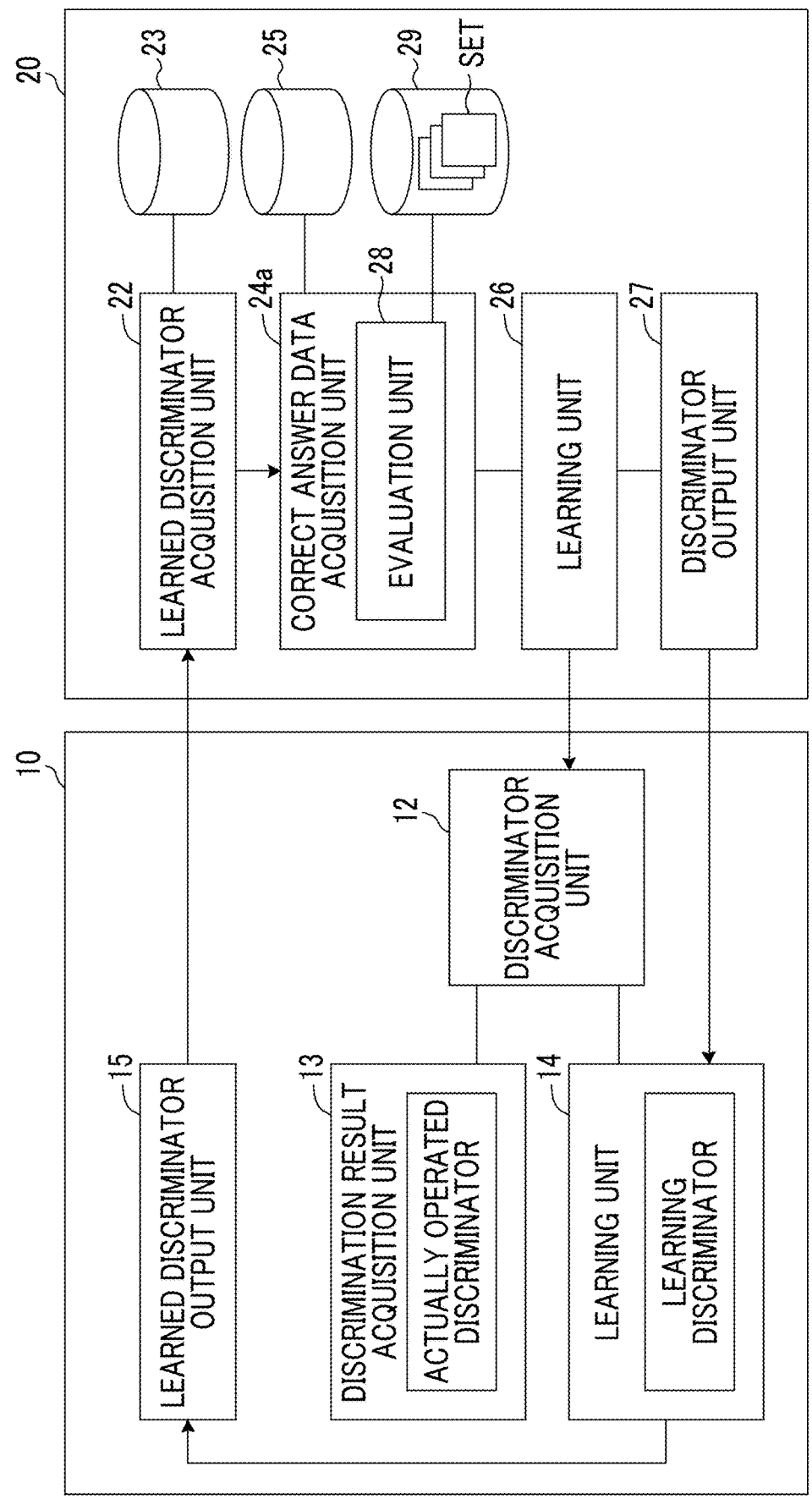
FIG. 7 is a block diagram illustrating a schematic configuration of a terminal device and a learning assistance device according to a second embodiment.

Next, a second embodiment will be described. The second embodiment is different from the first embodiment in the method of determining the correct answer data. Since a schematic configuration of the learning assistance system 1 is the same as that of the first embodiment, detailed description thereof will be omitted. FIG. 7 is a block diagram illustrating a schematic configuration of a terminal device 10 and a learning assistance device 20 according to the second embodiment. The same configurations as those of the first embodiment are denoted by the same reference numerals as those of the first embodiment, detailed description thereof will be omitted, and only different configurations will be described.

As illustrated in FIG. 7, the terminal device 10 includes a discriminator acquisition unit 12, a discrimination result acquisition unit 13, a learning unit 14, and a learned discriminator output unit 15. The learning assistance device 20 includes a learned discriminator acquisition unit 22, a discriminator storage unit 23, a correct answer data acquisition unit 24a, a correct answer data storage unit 25, a learning unit 26, and a discriminator output unit 27. A configuration of the terminal device 10 is the same as that of the first embodiment except that the correct answer data acquisition unit 24a of the learning assistance device 20 includes an evaluation unit 28 and an evaluation image storage unit 29.

In the case where the correct answer data is determined by majority vote, sufficient learning may be performed in each terminal device 10 as in the first embodiment, but for example, in a case where a discriminator not additionally learned in the terminal device 10 is received as the learned discriminator or in a case where a learned discriminator with a small number of additional learnings is used, a determination result is likely to be the same for the same input image data P, and a determination result of the discriminator in which such learning is not sufficiently performed is highly likely to be the correct answer data.

Therefore, the learning assistance device 20 evaluates the learned discriminators collected from the respective terminal device 10 in advance. The learning assistance device 20 sets a plurality of cases of disease covering a representative case pattern and also having correct answer data for image data as an evaluation image set SET, and the evaluation unit 28 evaluates the learned discriminators sent from the respective terminal devices 10 using the image set SET, and determines the weight of the discriminator according to a height of the correct answer rate. Further, since software intended for medical purposes is a target of the Pharmaceutical and Medical Device Act (the revised Pharmaceutical Affairs Act), the software is required to meet a criterion prescribed in the Pharmaceutical and Medical Device Act. Therefore, it is preferable for an evaluation image set SET formed through a combination of a plurality of images in which the criterion prescribed in the Pharmaceutical and Medical Device Act can be evaluated to be stored in the storage (the evaluation image storage unit 29) in advance. However, this evaluation image set SET is not sufficient for use in deep learning.

The weights are determined for the respective learned discriminators collected from the terminal device 10 according to the correct answer rate of the evaluation image set, the weights of the learned discriminators having the same result among the discrimination results are added, and the discrimination result having the largest added weight is set as correct answer data of the input image.

Since a flow of the deep learning process is the same as that of the first embodiment, the flow will be omitted.

Figure 8:
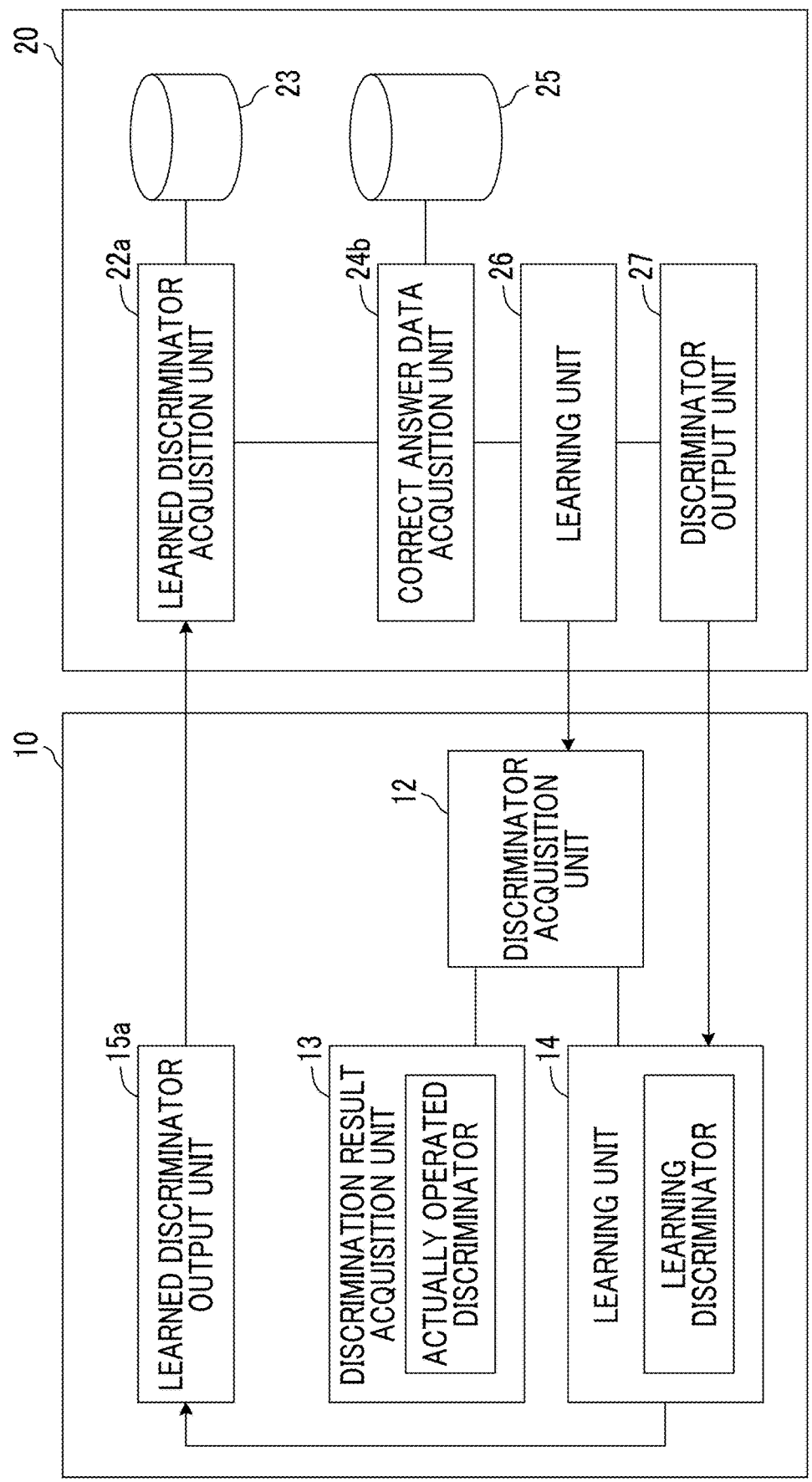
FIG. 8 is a block diagram illustrating a schematic configuration of a terminal device and a learning assistance device according to a third embodiment.

Next, a third embodiment will be described. The third embodiment is different from the first and second embodiments in the method of determining the correct answer data. Since a schematic configuration of the learning assistance system 1 is the same as that of the first embodiment, detailed description thereof will be omitted. FIG. 8 is a block diagram illustrating a schematic configuration of a terminal device 10 and a learning assistance device 20 according to the third embodiment. The same configurations as those of the first embodiment are denoted by the same reference numerals as those of the first embodiment, detailed description thereof will be omitted, and only different configurations will be described.

As illustrated in FIG. 8, the terminal device 10 includes a discriminator acquisition unit 12, a discrimination result acquisition unit 13, a learning unit 14, and a learned discriminator output unit 15a. The learning assistance device 20 includes a learned discriminator acquisition unit 22a, a discriminator storage unit 23, a correct answer data acquisition unit 24b, a correct answer data storage unit 25, a learning unit 26, and a discriminator output unit 27. The learned discriminator output unit 15a of the terminal device 10, and the learned discriminator acquisition unit 22a and the correct answer data acquisition unit 24b of the learning assistance device 20 are different from those of the first embodiment.

As in the second embodiment, even in a case where the performance of the learned discriminator is evaluated, evaluation results using the evaluation image set may be insufficient in a case where there is a problem with the number of cases of disease for evaluation of the learning assistance device 20 or coverage of the cases of disease. However, in a case where the learned discrimination learns a certain number of pieces of image correct answer data, it can be presumed that the performance is improving as appropriate.

Therefore, in a case where the learned discriminator output unit 15a of the terminal device 10 transmits the parameter of the learned discriminator, the learned discriminator output unit 15a of the terminal device 10 transmits the number of pieces of image correct answer data learned by the learned discriminator to the learning assistance device 20.

The learned discriminator acquisition unit 22a of the learning assistance device 20 receives the number of pieces of image correct answer data learned by the learned discriminator at each terminal device 10 together in a case where the learned discriminator acquisition unit 22a of the learning assistance device 20 receives the parameter. The weight is determined so that the weight increases as the number of pieces of image correct answer data learned by the correct answer data acquisition unit 24b and the learned discriminators of each terminal device 10 increases. The weights of the learned discriminators having the same discrimination result are added, and the discrimination result with the largest added weight is set as the correct answer data of the input image.

Since a flow of deep learning process is the same as that of the first embodiment, description thereof is omitted.

Next, a fourth embodiment will be described. The fourth embodiment is different from the first, second, and third embodiments in the method of determining the correct answer data. Since a schematic configuration of the learning assistance system 1 is the same as that of the first embodiment, detailed description thereof will be omitted. FIG. 9 is a block diagram illustrating a schematic configuration of a terminal device 10 and a learning assistance device 20 according to the fourth embodiment. The same configurations as those of the first embodiment are denoted by the same reference numerals as those of the first embodiment, detailed description thereof will be omitted, and only different configurations will be described.

As illustrated in FIG. 9, the terminal device 10 includes a discriminator acquisition unit 12, a discrimination result acquisition unit 13, a learning unit 14, and a learned discriminator output unit 15b. The learning assistance device 20 includes a learned discriminator acquisition unit 22b, a discriminator storage unit 23, a correct answer data acquisition unit 24c, a correct answer data storage unit 25, a learning unit 26, and a discriminator output unit 27. The learned discriminator output unit 15b of the terminal device 10 and the learned discriminator acquisition unit 22b and the correct answer data acquisition unit 24c of the learning assistance device 20 are different from those of the first embodiment.

The number of pieces of image correct answer data for each type of cases of disease is biased due to the characteristics of the medical facility, the regional nature, or the like, and the number of pieces of image correct answer data is small in any kind of diseases even though the number of all pieces of image correct answer data is large, the performance is likely not to be improved in the disease. Therefore, the number of pieces of image correct answer data learned by the learned discriminator of each medical facility is received from each terminal device 10 for each type of cases of disease.

Therefore, in a case where the learned discriminator output unit 15b of the terminal device 10 transmits the parameter of the learned discriminator, the learned discriminator output unit 15b of the terminal device 10 transmits the number of pieces of image correct answer data for each type of cases of disease learned by the learned discriminator to the learning assistance device 20. Specifically, it is determined which case of disease the image correct answer data learned by the learning unit 14 of the terminal device 10 relates to, for example, on the basis of a DICOM tag attached to the image of image correct answer data, and the number of learned image correct answer data is changed for each type of cases of disease. The type of cases of disease is classified by disease name (which may be an image diagnostic name in case of image inspection) or a type of disease name. In a case where a plurality of organs are collectively processed by one discriminator, an organ name may be used.

The learned discriminator acquisition unit 22b of the learning assistance device 20 receives the number of pieces of image correct answer data for each type of cases of disease learned by the learned discriminator at each terminal device 10 in a case where the learned discriminator acquisition unit 22b of the learning assistance device 20 receives the parameter.

In the correct answer data acquisition unit 24c, it is estimated that the performance of the learned discriminator is higher as the number of learned image correct answer data is larger. To reflect this, the number of pieces of image correct answer data learned by each facility for each type of cases of disease is counted for the learned discriminator of each terminal device 10, and, the weight for each type of cases of disease is determined for each learned discriminator so that weight is increased as the number increases. In addition, weights of the learned discriminators having the same discrimination result are added in correspondence to the type of cases of disease of the input image, and the discrimination result having the largest added weight is set as the correct answer data of the input image.

Since a flow of deep learning process is the same as that of the first embodiment, description thereof will be omitted.

With a scheme according to the embodiment, it is possible to evaluate the learned discriminator in consideration of, the number of pieces of image correct answer data of each medical facility, the type of cases of disease, and the like.

Further, the evaluation image set according to the second embodiment may be set as an evaluation image set capable of evaluating a discriminator for each type of disease, and the weight of the learned discriminator of each terminal device may be determined according to the correct answer rate for each type of disease. The weights of the learned discriminators having the same discrimination result may be added according to the type of cases of disease of the input image, and the discrimination result having the largest added weight may be set as the correct answer data of the input image.

Further, although the weight is automatically determined in the fourth embodiment, the weight may be determined manually and stored in the learning assistance device 20 in advance in consideration of importance of the facility, a confident disease of each facility, or the like.

Although the embodiment in which the learning assistance device 20 and the terminal device 10 are connected via the network has been described in the above description, an image processing program incorporating a discriminator functioning as an actually operated discriminator and a learning program incorporating a discriminator functioning as a learning discriminator may be stored in a recording medium such as a DVD-ROM and distributed to each medical institution, instead of over the network.

In this embodiment, the discriminator acquisition unit 12 of the terminal device 10 reads the image processing program and the learning program from the DVD-ROM to the terminal device 10 and installs the image processing program and the learning program, and reads the identification information ID of the image correct answer data used for learning of the learning discriminator from the recording medium. Further, the learned discriminator output unit 15 of the terminal device 10 records the parameter of the learned discriminator in the DVD-ROM, and distributes the parameter to an operator of the learning assistance device 20 by mailing or the like.

Further, the learned discriminator acquisition unit 22 of the learning assistance device 20 reads the parameters of the learned discriminator recorded on the DVD-ROM. Furthermore, the discriminator output unit 27 of the learning assistance device 20 records the image processing program and the learning program on a DVD-ROM and sends the image processing program and the learning program to an operator of the terminal device 10 by mailing or the like.

As described in detail above, in the present invention, accurate correct answer data of an image is automatically generated using a discriminator of which the performance has been improved using the medical images stored in each medical institution. Thus, it is possible to use a large amount of medical images for deep learning.

Although the case where the learning assistance device and the terminal device function on a general-purpose computer has been described above, a dedicated circuit such as an application specific integrated circuit (ASIC) or field programmable gate arrays (FPGA) that permanently stores a program for executing some of functions may be provided. Alternatively, a program instruction stored in a dedicated circuit and a program instruction executed by a general-purpose CPU programmed to use a program of a dedicated circuit may be combined. As described above, the program instructions may be executed through any combination of hardware configurations of the computer.

What is claimed is:

1. A learning assistance system comprising a learning assistance device and terminal devices connected over a network,
wherein each of the terminal devices comprises a processor configured to output a learned discriminator to the learning assistance device over the network, the learned discriminator being obtained at each of the terminal devices by causing a learning discriminator to perform learning using an image and correct answer data thereof that are stored in a database of each of the terminal devices,
the learning assistance device comprises a processor configured to:
acquire the learned discriminators from the terminal devices over the network;
acquire discrimination results obtained by causing the learned discriminators to discriminate the same input image at the learning assistance device, each of the discrimination results being obtained from each of the learned discriminators;
determine correct answer data of the same input image on the basis of the discrimination results; and
output a new learning discriminator to each of the terminal devices over the network, the new learning discriminator being obtained by causing the learning discriminator to perform learning at the learning assistance device by using the same input image and the determined correct answer data.

2. The learning assistance system according to claim 1, wherein the processor of each of the terminal devices device is configured to acquire the new learning discriminator from the learning assistance device over the network and obtain a new learned discriminator as the learned discriminator by causing the new learning discriminator to perform learning at each of the terminal devices by using an image and correct answer data thereof that are stored in the database of each of the terminal devices.

3. The learning assistance system according to claim 1, wherein the processor of each of the terminal devices is configured to:
acquire an actually learned operated discriminator learned at the learning assistance device by using the same image and correct answer data of the same image as those of the learning discriminator; and
acquire a discrimination result of discriminating an image that is a discrimination target using the actually operated discriminator.

4. The learning assistance system according to claim 1, wherein the processor of each of the terminal devices is further configured to:
acquire an actually operated discriminator from the learning assistance device over a network, the actually operated discriminator being learned at the learning assistance device by using the same image and correct answer data of the same image as those of the learning discriminator, and
acquire a discrimination result of discriminating an image that is a discrimination target using the actually operated discriminator.

5. The learning assistance system according to claim 1, wherein the processor of each of the terminal devices is further configured to:
acquire a new actually operated discriminator from the learning assistance device over a network, the actually operated discriminator being learned at the learning assistance device by using the same input image and the determined correct answer data as those of the new learning discriminator, and
acquire a discrimination result of discriminating an image that is a discrimination target using the new actually operated discriminator.

6. The learning assistance system according to claim 1, wherein the processor of the learning assistance device is configured to output an actually operated discriminator learned using the same input image and the determined correct answer data, to each of the terminal devices over the network.

7. The learning assistance system according to claim 1, wherein the processor of the learning assistance device is configured to determine a discrimination result having the largest number of same results among the discrimination results, as correct answer data of the same input image.

8. The learning assistance system according to claim 1, wherein the processor of the learning assistance device is configured to:
determine a weight of each of the learned discriminators according to each of the terminal devices;
add the weights of learned discriminators having the same result among the discrimination results; and
set a discrimination result having the largest added weight as correct answer data of the same input image.

9. The learning assistance system according to claim 1, wherein the processor of the learning assistance device is configured to:
determine a weight of each of the learned discriminators according to the number of pieces of correct answer data learned by the learned discriminator at each of the terminal devices;
add the weights of learned discriminators having the same result among the discrimination results; and
set a discrimination result having the largest added weight as correct answer data of the same input image.

10. The learning assistance system according to claim 1, wherein the processor of the learning assistance device is configured to:
determine weights for types of cases of disease of the image learned by each of the learned discriminators with respect to each of the learned discriminators,
add the weights corresponding to the types of cases of disease of the image of learned discriminators having the same result among the discrimination results; and
set a discrimination result having the largest added weight as correct answer data of the same input image.

11. The learning assistance system according to claim 1, wherein the processor of the learning assistance device is configured to:
evaluate a correct answer rate using an image set including images with respect to each of the learned discriminators;
determine a weight of each of the learned discriminators according to the correct answer rate;
add the weights of learned discriminators having the same discrimination results among the discrimination results; and
set a discrimination result having the largest added weight as correct answer data of the same input image.

12. A terminal device comprising a processor configured to:
acquire a learning discriminator and a learned actually operated discriminator from a learning assistance device, the learned actually operated discriminator being learned using the same image and correct answer data of the same image as those of the learning discriminator;
acquire a discrimination result of discriminating an image that is a discrimination target using the actually operated discriminator; and
output a learned discriminator to a learning assistance device, the learned discriminator being obtained by causing the learning discriminator to perform learning at the terminal devices by using an image and correct answer data thereof that are stored in a database of the terminal device.

13. The terminal device according to claim 12,
wherein the processor is configured to acquire the learning discriminator and the actually operated discriminator from the assistance device over a network, and
the processor is configured to send and output the learned discriminator over the network.

14. The terminal device according to claim 12,
wherein the processor is configured to receive a new learning discriminator, the new learning discriminator being obtained at the learning assistance device by causing the learning discriminator to perform learning using the same input image and determined correct answer data, the determined correct answer data being determined by the learning assistance device on the basis of the discrimination results, and the discrimination results being acquiring by causing learned discriminators including the learned discriminator to discriminate the same input image.

15. The terminal device according to claim 14,
wherein the processor is configured to receive a new actually operated discriminator from the learning assistance device, the actually operated discriminator learning the same input image and the determined correct answer data.

16. A method for operating a learning assistance system comprising a learning assistance device and terminal devices connected over a network,
the method comprising:
acquiring learned discriminators from the terminal devices over the network at the learning assistance device, each of the learned discriminators being obtained by causing a learning discriminator to perform learning at each of the terminal devices by using an image and correct answer data thereof;
acquiring discrimination results obtained by causing the learned discriminators to discriminate the same input image at the learning assistance device, each of the discrimination results being obtained from each of the learned discriminators;
determining correct answer data of the same input image on the basis of the discrimination results at the learning assistance device; and
outputting a new learning discriminator from the learning assistance device to each of the terminal devices over the network, the new learning discriminator being obtained by causing the learning discriminator to perform learning at the learning assistance device by using the same input image and the determined correct answer data.

17. A non-transitory computer-readable recording medium storing therein a learning assistance program causing a computer to perform the method according to claim 16.

18. A method for operating a learning assistance system comprising a learning assistance device and terminal devices connected over a network, the method, comprising:
acquiring a learning discriminator and a learned actually operated discriminator from the learning assistance device over the network at each of the terminal devices, the learned actually operated discriminator being learned by using the same image and correct answer data of the same image as those of the learning discriminator;
acquiring a discrimination result of discriminating an image that is a discrimination target using the actually operated discriminator at each of the terminal devices; and
outputting a learned discriminator from each of the terminal devices to a learning assistance device, the learned discriminator being obtained by causing the learning discriminator to perform learning at each of the terminal devices by using an image and correct answer data thereof that are stored in a database of the terminal device.

19. A non-transitory computer-readable recording medium storing therein a program causing a computer to perform the method according to claim 18.

* * * * *